(12) United States Patent
Walter et al.

(10) Patent No.: US 6,253,653 B1
(45) Date of Patent: Jul. 3, 2001

(54) DISC-MICROTOME

(75) Inventors: Roland Walter, Altlussheim; Manfred Biehl, Meckesheim; Juergen Vierling, Eppelheim; Andreas Laudat, Hirschberg; Peter Scheck, Rauenberg; Rolf Metzner, Dossenheim, all of (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 09/230,584

(22) PCT Filed: Jul. 26, 1997

(86) PCT No.: PCT/DE97/01579

§ 371 Date: Jan. 29, 1999

§ 102(e) Date: Jan. 29, 1999

(87) PCT Pub. No.: WO98/04898

PCT Pub. Date: Feb. 5, 1998

(30) Foreign Application Priority Data

Jul. 29, 1996 (DE) ................................ 196 30 382
Jul. 29, 1996 (DE) ......................... 296 12 938 U (51) Int. Cl.⁷ .................................................. B23D 19/00
(52) U.S. Cl. ............................... 83/703; 83/733; 83/856; 83/915.5
(58) Field of Search ................... 83/915.5, 856, 83/170, 403.1, 403, 410.8, 410.9, 411.3, 267, 703, 733

(56) References Cited

U.S. PATENT DOCUMENTS

| | | | |
|---|---|---|---|
| 1,928,689 | * 10/1933 | Heys | 83/411.3 |
| 2,753,761 | 7/1956 | Hillier | 88/40 |
| 2,795,998 | * 6/1957 | Gorham et al. | 83/411.3 |
| 2,875,669 | * 3/1959 | Sjostrand et al. | 83/411.3 |
| 3,191,477 | * 6/1965 | Danon | 83/267 |
| 3,611,875 | * 10/1971 | Wistedt | 83/915.5 |

(List continued on next page.)

FOREIGN PATENT DOCUMENTS

| | | | |
|---|---|---|---|
| 172605 | 9/1952 | (AT) | |
| 282994 | 7/1970 | (AT) | |
| 263871 | 9/1912 | (DE) | |
| 5620 | 7/1954 | (DE) | |
| 26 40 966 | 3/1978 | (DE) | |
| 31 36 770 | 3/1983 | (DE) | |
| 31 44 120 | 5/1983 | (DE) | |
| 195 31 524 | 7/1996 | (DE) | |
| 654123 | 6/1951 | (GB) | |
| 153381 | * 3/1961 | (SU) | 83/915.5 |

OTHER PUBLICATIONS 42h. 1 670 514 Sartorius–Werke A.G., Goettingen, "Zustelleinrichtung fuer Mikrotome", May 17, 1951, S 3722 (T. 4; Z. 1).

Isamu Tamura et al, "Rotor Slicer" Japanese Pat. No. 63–241442, Oct. 6, 1988, Patents Abstracts of Japan.

LEICA SP1600—Saw Microtome Instruction Manual, 11/86.

*Primary Examiner*—Rinaldi I. Rada
*Assistant Examiner*—Omar Floves-Sáchez
(74) *Attorney, Agent, or Firm*—Foley & Lardner (57) ABSTRACT

The invention relates to a microtome (1) for producing thin slices for microscopy, which is provided with a base (2), a blade holder (3) for holding a cutting blade (4) and an object holder (5) for holding the object (6) to be cut. Cutting occurs in a plane by a relative movement between the object (6) and the cutting blade (4) To produce the relative movement, a rotating component (7) is provided with a drive motor (17), wherein the rotating axis of the rotating component (7) is arranged obliquely to the base (2), and a feed slide (9) is provided with a linear guide for setting the slice thickness. The structure of said feed slide (9) is such that it is removable via a feed motor (17) and a control circuit (14) connected thereto.

32 Claims, 4 Drawing Sheets

U.S. PATENT DOCUMENTS

| | | | |
|---|---|---|---|
| 3,884,563 | 5/1975 | Evans et al. | 352/131 |
| 3,902,390 | 9/1975 | Darbo | 83/170 |
| 4,060,440 * | 11/1977 | Behme et al. | 83/915.5 |
| 4,377,958 * | 3/1983 | Leighton | 83/915.5 |
| 5,161,446 * | 11/1992 | Holbl et al. | 83/915.5 |
| 5,226,335 * | 7/1993 | Sitte et al. | 83/915.5 |
| 5,299,481 * | 4/1994 | Lihl et al. | 83/915.5 |
| 5,461,953 * | 10/1995 | McCormick | 83/915.5 |
| 5,535,654 * | 7/1996 | Niesporek et al. | 83/915.5 |
| 5,671,648 | 9/1997 | Dern | 83/411.1 |
| 5,713,255 * | 2/1998 | Izvozichikov et al. | 83/915.5 |
| 5,761,977 * | 6/1998 | Jakobi et al. | 83/915.5 |
| 5,974,934 * | 11/1999 | Woods | 83/932 |

* cited by examiner

DISC-MICROTOME

BACKGROUND OF THE INVENTION

The invention relates to a microtome.

DE 31 44 120 A1 has disclosed a traversing microtome which contains a base and a carriage which can be moved along slide rails. The cutting blade is in this case fixed immovably to the base, while the specimen holder is arranged on the carriage. In order to make the cut, the carriage is moved manually along its guide on the base.

However, traversing microtomes are also known in which the cutting blade is mounted on the carriage and the specimen holder is mounted in a fixed position on the base.

In both types of traversing microtome, the specimen is cut by way of a relative movement between the cutting blade and the object.

Another type of microtome is known from DE 195 31 524 C1. The rotary microtome described in this document has an object carriage on which there is an object holder for the specimen which is to be cut. The object holder is moved up and down on the rotary microtome in a vertical path. During this movement, the specimen is guided past a blade which is arranged in a fixed position on the rotary microtome.

In this case too, the specimen is cut by way of a relative movement between the cutting blade and the object. In both types of known microtome, it is necessary to return the object or the cutting blade to the starting position after a cutting operation has taken place. During this return movement, it is imperative that the cutting blade does not collide with the specimen if clean specimen cuts are to be produced. In both cases, this is achieved by the cutting blade or the specimen being retracted a certain amount by means of a feed device, so that the moving component can be moved past the fixed component. In the event of a further cutting operation, the specimen or the cutting blade is advanced again by this certain amount plus the cut thickness set.

Both types of microtome have proven themselves in practice. The need for a return movement to a starting position after a cutting operation has taken place means that microtomes of this nature are unable to achieve rapid cutting sequences. In addition, these oscillating movements result in considerable forces during the acceleration or deceleration of the moving components, and these oscillations have to be compensated for, entailing a high level of mechanical outlay. Otherwise, there is a risk of vibrations being transmitted to the microtome, resulting in unusable thin-cut sections.

The document "Leica SP 1600—Saw Microtome, Instruction Manual, V0.0 English—11/86, from Leica Instruments GmbH" has disclosed a saw microtome for cutting very hard objects, such as bones, ceramic, etc. As its cutting blade, the saw microtome has a diamond-tipped annular saw which rotates at 600 rpm. The object to be cut is arranged, together with the object holder, on a rotationally movable arm. The arm is pivoted extremely slowly toward the annular saw in order to carry out a sawing cut. Following the sawing cut, the arm has to be moved back again. This microtome does not allow continuous cutting or the cutting of tissue samples.

DE 26 40 966 A1 and JP 63-241442 A have disclosed cutting devices in which a disk-like cutting blade is driven by a motor. Arrangement [sic] of this nature are used to produce thin-cut sections of very hard materials, such as bone.

DE-C 263 871 has disclosed a microtome with a fixed blade and a rotating object holder. The cutting blade is arranged in a blade holder which is fed onto the object holder using mechanical means for setting the cut thickness. A simple crank handle is used to drive the microtome described.

AT 172 605 and U.S. Pat. No. 3,191,477 have each disclosed a microtome with a rotatably mounted disk. A specimen holder is arranged on the end side of the disk, so that the axis of rotation of the disk is approximately perpendicular to the cutting plane. In this arrangement, the object is guided past the cutting blade along an orbital path, so that the cut section acquires a cylindrical profile. However, in many cases this cylindrical profile cannot be used during a subsequent microscopic examination, since the cut section has to be placed flat beneath the microscope.

DD 5 620 has disclosed a motor-driven, revolving blade carrier in which the object holder is advanced by means of an eccentric disk and a lever which acts thereon. This arrangement provides for a parallel arrangement of object and blade during the cutting operation. However, the object is advanced not by means of a linear component but rather using a lever and an eccentric disk.

U.S. Pat. No. 3,884,563 describes a microtome with a motor-driven, revolving blade carrier in which the object holder is advanced by means of a carriage. The microtome also has a cryostat and a film camera which is used to film the specimen during the cutting operation. In this microtome, the cut sections are not examined further, but rather are disposed of via a collection container.

U.S. Pat. No. 2,753,761 and GB-C 654 123 describe disk microtomes in which the object holder is arranged on a disk and the blade holder is arranged fixedly on the microtome. In this case, the cutting advance takes place by way of a parallel displacement of the disk with respect to the base, using a thermocouple and a spindle, or by way of a parallel displacement of the blade holder on the base. There is no provision in these documents for motor-controlled feed.

U.S. Pat. No. 3,902,390 has disclosed a pocket microtome in which the cutting blade is arranged on a rotationally moveable arm and can be manually preloaded by means of a spring. This microtome is designed for portable use and is unsuitable for carrying out series of cuts.

SUMMARY OF THE INVENTION

Therefore, the object of the present invention is to optimize the relative movement between the cutting blade of the microtome and the object and, in so doing, to ensure a rapid and accurate sequence of cuts.

As a result of the rotating component on which either the object or the cutting blade is arranged there is no need for the blade or the object to be moved back following a first cutting operation. This eliminates the need for the reversing movement in order for the microtome to return to its starting position, and the mechanical outlay on avoiding vibrations can be minimized.

A further advantage lies in the fact that, in contrast to the known disk microtomes, a motor-controlled feed is provided for setting the cut thickness. A control circuit also allows different cut thicknesses to be preselected for a single specimen.

In a further configuration of the invention, there is provision for a plurality of object holders to be arranged on the rotating component, in order to carry out a plurality of cutting operations simultaneously. In this case, the object holders, together with the objects to be cut, may be grouped together next to one another on the outer circumference of the rotating component or next to one another in the direction of the center of the disk.

Providing a plurality of objects also makes it possible to cut into these objects together in a first phase, i.e. all the objects are cut during a single revolution of the component.

Arranging an angle-position encoder on the rotating component allows the position of the objects with respect to the cutting blade to be determined. It is then possible to use the control circuit to individually preselect the cutting sequence and the cut thickness for each single object. However, a precondition for this individual preselection is that it be possible to change the distance between the cutting blade and the object during operation. This is achieved by using the angle position encoder to determine the disk position and using the motor-driven feed and the control circuit to change the position of the cutting blade or of the object while the rotating disk is running.

As a result, the control circuit can be used to individually preselect the sequence of specimens to be cut and, in addition, to individually set an appropriate cut thickness.

BRIEF DESCRIPTION OF THE DRAWINGS

The invention is explained in more detail using exemplary embodiments and with reference to the diagrammatic drawing, in which:

FIG. 2b: shows a front view of the disk microtome in accordance with FIG. 2a

FIG. 7b: shows a front view of the disk microtome in accordance with FIG. 7a

DETAILED DESCRIPTION OF THE PREFERRED EMBODIMENTS

Figure 1A:
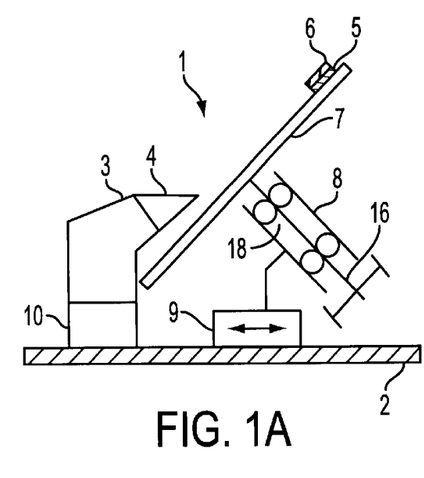
FIG. 1a: shows a side view of the disk microtome with a fixed blade holder and a horizontally displaceable disk

FIG. 1a shows a side view of a disk microtome 1 with a base 2 and a support part 10 which is arranged on the base 2 and supports a blade holder 3 for holding a cutting blade 4. Furthermore, a feed carriage 9, which is designed so that it can move in the direction of the double arrow, is arranged on the base 2. The feed carriage 9 supports a frame 8 to which a rotating component 7, in the form of a disk, is rotatably attached by means of a rotary shaft 16 and a rolling bearing. An object holder 5 for holding an object 6 which is to be cut is arranged eccentrically on the disk 7. Displacing the feed carriage 9 allows the distance between the fixed cutting blade 4 and the disk 7 or the object 6 to be changed. The mutually adapted angular arrangement of the cutting blade 4 and the disk 7 with respect to the base 2 means that the disk surface or the specimen 6 is always adjusted parallel to the cutting edge of the blade 4 during this adjustment.

Figure 1B:
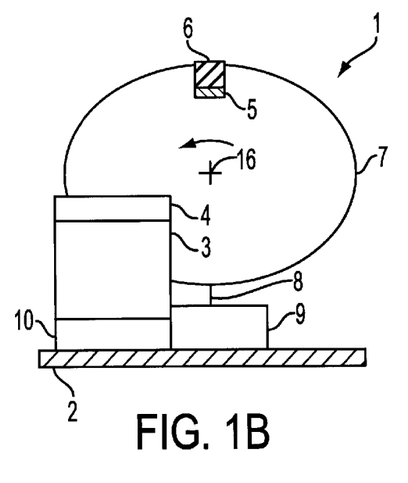
FIG. 1b: shows a front view of the disk microtome in accordance with FIG. 1a FIG. 2a: shows a side view of the disk microtome with a fixed blade holder and a vertically displaceable disk.

FIG. 1b shows a front view of the arrangement in accordance with FIG. 1a. It is clear from this view that the object 6 is guided past the cutting blade 4 in the direction of the arrow by the rotation of the disk 7, and in this way the cut thickness set by means of the feed carriage 9 is removed from the object 6. After a cutting operation has been completed, the disk 7 continues to rotate in the direction of the arrow, and during this rotational movement the disk 7 is moved toward the cutting blade 4 by means of the feed device 9. The feed movement always takes place after a cutting operation has been carried out.

Figure 2A:
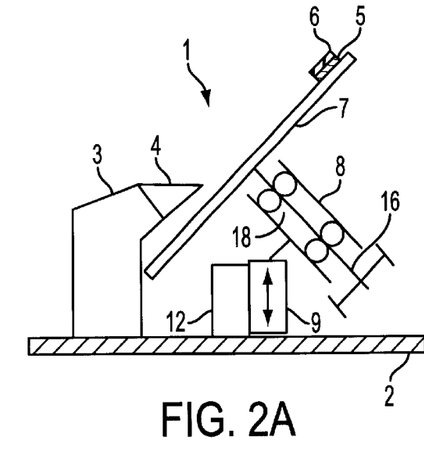

FIG. FIG. 2a shows a side view of the disk microtome 1 in a similar manner to FIG. 1a, but in this case the feed carriages [sic] 9 is arranged on a pedestal 12 and is mounted so that it can be displaced vertically with respect to the base 2 in the direction of the double arrow. The pedestal 12 is attached to the base 2 of the disk microtome 1.

Figure 2B:
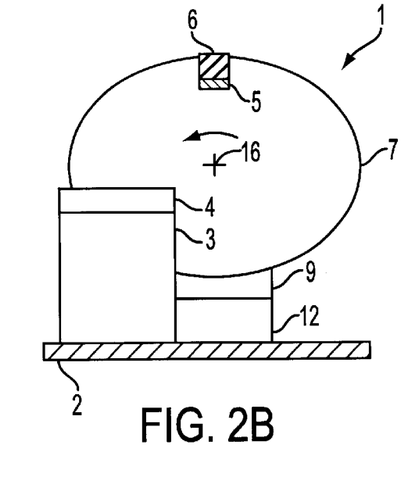

FIG. 2b shows a side view of FIG. FIG. 2a, with the pedestal 12 and the feed carriage 9. In this exemplary embodiment, the disk 7 or the object 6 is again moved parallel to the cutting edge of the blade 4.

Figure 3A:
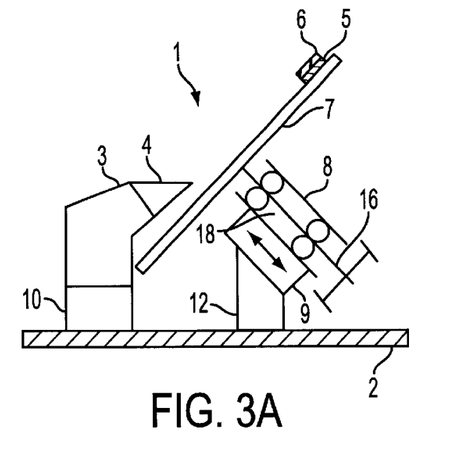
FIG. 3a: shows a side view of the disk microtome with a fixed blade holder and a disk which can be displaced along the axis of rotation

FIG. 3a shows a side view of the disk microtome 1, in a similar manner to FIGS. 1a and 2a, but in this exemplary embodiment the feed carriage 9 is arranged on the frame 8 directly and parallel to the rotary shaft 16. The feed carriage 9 is supported by the pedestal 12, which is attached to the base 2 in a fixed position. In this arrangement, the rotary shaft 16 of the disk 7 simultaneously corresponds to the direction of displacement of the disk 7 in the direction of the double arrow.

Figure 3B:
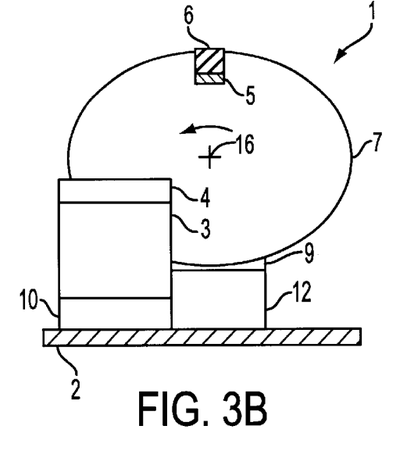
FIG. 3b: shows a front view of the disk microtome in accordance with FIG. 3a FIG. 4a: shows a side view of the disk microtome with a blade holder which can be displaced parallel to the axis of rotation of the disk

FIG. 3b shows a side view of FIG. 3a, with the pedestal 12 and the feed carriage 9, the disk 7 or the object 6 being moved parallel to the cutting edge of the blade 4 using the feed carriage 9.

Figure 4A:
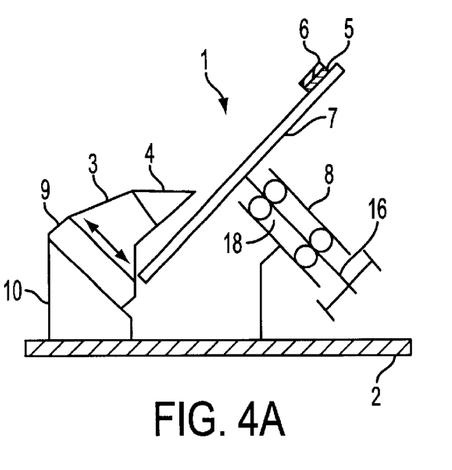

FIG. 4a shows a side view of the disk microtome 1 with the frame 8 arranged in a fixed position on the base 2, which frame supports the disk 4 [sic] with the object holder 5 and the object 6. Together with the cutting blade 4, the blade holder 3 is attached to the feed carriage 9 in such a manner that it can be displaced in the direction of the double arrow, the feed carriage 9 being arranged on a support part 10. The support part 10 is arranged in a fixed position on the base 2 of the microtome 1. Owing to the angled-off form of the support part 10, the direction of displacement of the blade holder 3 coincides with the rotary shaft 16 of the disk 4 [sic], so that the cutting edge of the blade 4 can be advanced parallel to the surface of the disk 4 [sic].

Figure 4B:
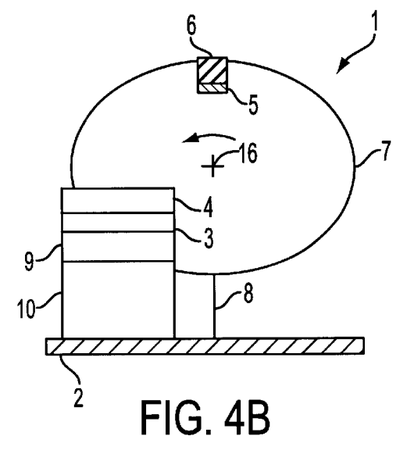
FIG. 4b: shows a front view of the disk microtome in accordance with FIG. 4a FIG. 5a: shows a side view of the disk microtome with a blade holder which can be displaced vertically

FIG. 4b shows a side view of FIG. 4a, with the support part 10, the feed carriage 9 arranged thereon, the blade holder 3 for holding the cutting blade 4. The frame 8 is fixedly connected to the base 2.

Figure 5A:
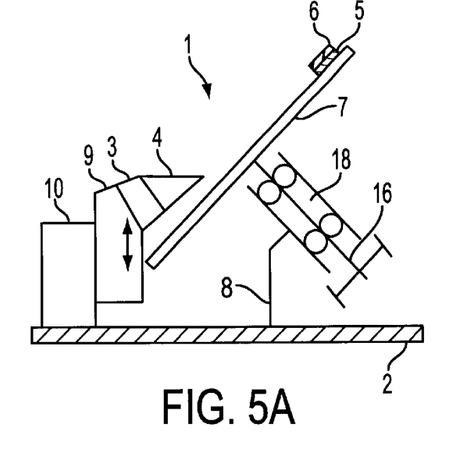

FIG. 5a shows a side view of the disk microtome in accordance with FIG. 4a, but in this case the feed carriage 9 is arranged on the support part 10 in such a manner that it can be moved vertically with respect to the base 2 of the disk microtome 1. This again ensures that the cutting edge of the blade 4 is designed so that it can be moved parallel to the disk 7 by means of the feed carriage 9.

Figure 5B:
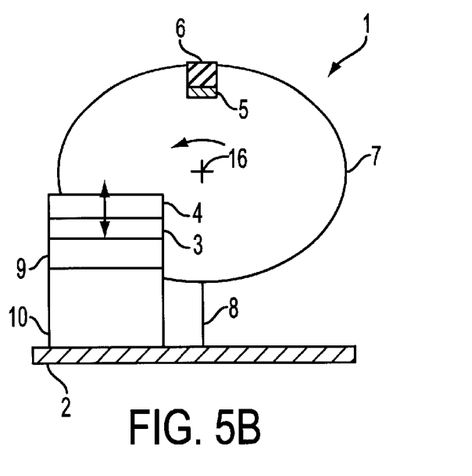
FIG. 5b: shows a front view of the disk microtome in accordance with FIG. 5a FIG. 6a: shows a side view of the disk microtome with a blade holder which can be displaced horizontally

FIG. 5b shows a front view of the microtome 1 in accordance with FIG. 5a, with the support part 10 and the blade holder 3 which is arranged thereon and is fitted so that it can be moved vertically with respect to the base 2.

Figure 6A:
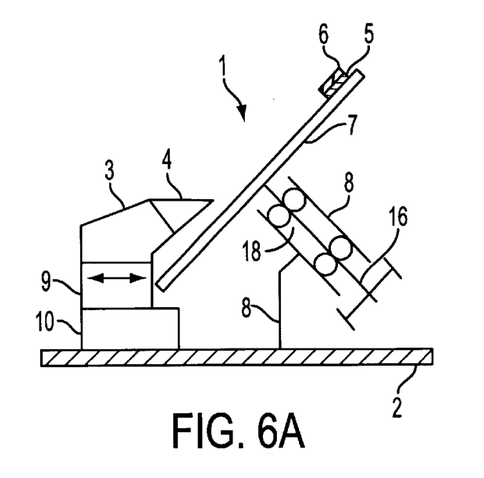

FIG. 6a shows a side view of the disk microtome 1 in accordance with FIGS. 4a and 5a, but in this case the feed carriage 9 is arranged on the support part 10 in such a manner that it can be displaced parallel to the base 2 of the disk microtome 1. Naturally, the feed carriage 9 may form a single structural unit with the support part 10 and, as illustrated in FIG. 1a, may be directly attached to the base 2 of the microtome 1.

Figure 6B:
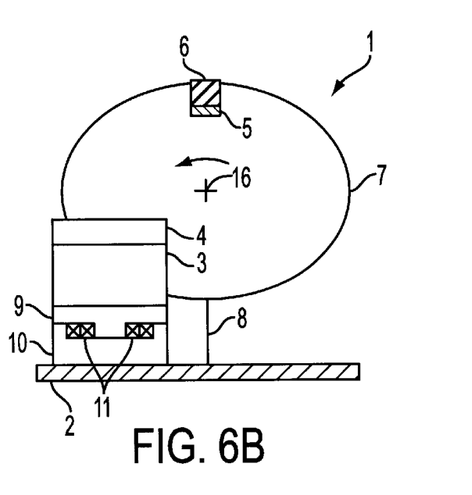
FIG. 6b: shows a front view of the disk microtome in accordance with FIG. 6a FIG. 7a: shows a side view of the disk microtome with a motor-driven feed, a control circuit, an angle position encoder and a plurality of objects arranged on the disk

FIG. 6b shows a front view of the disk microtome 1 in accordance with FIG. 6a, and in this case the linear guides 11, which are integrated in the feed carriage 9, for displacing the blade holder 3 are also shown. These linear guides 11 are, of course, also provided in all the other exemplary embodiments illustrated, for the purpose of moving the feed carriage 9, and are not shown in the other figures simply for reasons of clarity.

Figures 7A, 7B:
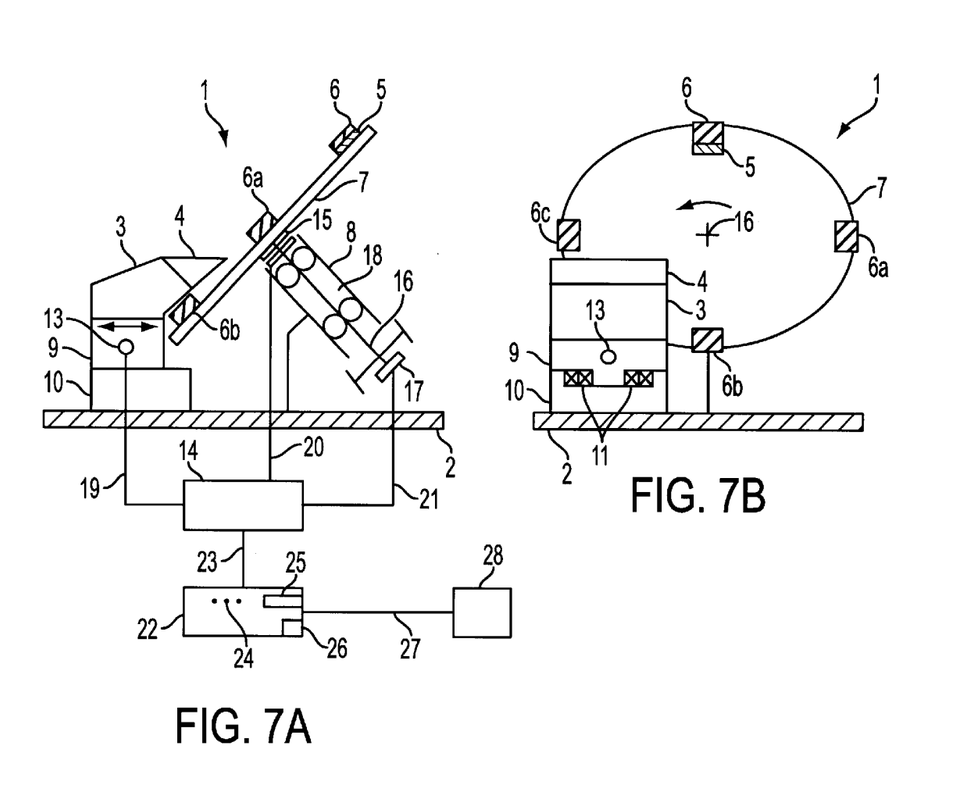

FIG. 7a shows a side view of the disk microtome 1 with a plurality of objects 6 and 6a–6c arranged on the disk 7. In this exemplary embodiment, which by way of example comprises the arrangement of the feed carriage 9 in accordance with the exemplary embodiment shown in FIG. 6a, the feed carriage 9 for the blade holder 3 can be moved by means of a motor-driven adjustment means 13. This drive motor 13, which is preferably designed as a stepper motor, is electrically connected to a control circuit 22 via a control line 19. An angle-position encoder 15 is arranged between the disk 7 and the frame 8, which encoder determines the current rotational position of the disk 7 with the objects 6 arranged thereon and, via a control line 20, transmits this data to the control circuit 14. A motor 17, which is likewise electrically connected to the control circuit 14 via a control line 21, is provided for the drive for the rotary shaft 16. Naturally, the angle-position encoder 15 for determining the position of the disk may also be integrated in the motor drive 17, and/or the motor 17 is designed as a stepper motor. In a further configuration of the invention, a light barrier can be used instead of the angle-position encoder 15 to detect the position of the object holder 5 with respect to the cutting blade.

An operating panel 22 is connected to the control circuit 14 via a control line 23, which operating panel is fitted with selection keys 24, a display device and an interface 26 for connection to an external computer 28 via a control line 27.

In order to cut the four objects 6–6c illustrated, whether simultaneously or successively, the stepper motor 13 is activated via the appropriate key 24 on the operating panel 22 so as to feed the blade 4 onto the surface of the objects 6–6c.

There may be provision for the disk 7, together with the preselected object holder 6, initially to rotate into the area of the cutting blade 4 and to stop in that area. The blade 4 is then fed onto the surface of the object 6 and, if necessary, realigned. In this case, there may be provision for this position to be stored in a reproducible manner. It is then possible to carry out this setting for a further object holder and in this case too to store the corresponding setting.

After the starting position of the cutting blade 4 has been reached, the drive motor 17 for the disk 7 is switched on by means of the operating panel 22 and the control circuit 14. After the motor 17 has reached its rated speed, which can be detected by the angle-position encoder 15, the servomotor 13 is supplied with current via the control circuit 14 in accordance with the cut thickness which has been preselected on the operating panel 22. After the object 6 has been cut or after all the objects 6 and 6a–6c have been cut, the stepper motor 13 is again supplied with current and the cutting blade 4 carries out a further feed movement toward the object(s) 6–6c. If a fixed amount is preselected on the operating panel 22 for cutting into the objects, the motor 13 is supplied with current in individual steps until the total magnitude of the preselected initial cut is reached.

Then, the operating panel 22 is used to preselect the appropriate cut thickness for the object 6 or the individual objects 6–6c, and this thickness is displayed on the display device 25. The actual cutting operation for producing the thin-cut sections can then be started.

The rotational speed of the disk 7 and hence the cutting speed can be determined using the angle-position encoder 15 and the control circuit 14. The cutting speed required for thin-cut sections of this nature is dependent on the cut thickness set, the specimen which is to be cut and the blade used. For this reason, there is provision for it to be possible to preselect a desired cutting speed using the operating panel 22. If this desired cutting speed is not maintained during the cutting operation, i.e. the angle-position encoder provides correspondingly fewer pulses during the cutting operation, the rotational speed of the motor 17 is automatically increased accordingly.

Moreover, monitoring the desired rotational speed of the disk 7 by means of the angle-position encoder 15 allows the feed of the cutting blade 4 for cutting into the object 6 to be simplified. The motor 13 of the feed carriage 9 is supplied with current until an initial cut into the object 6, and hence a slight deviation from the desired rotational speed/desired speed of the disk 7, are recorded by the angle-position encoder 15. This deviation is used as a signal for the beginning of the cutting operation and the desired rotational speed of the disk or the cutting speed is adapted accordingly.

After initial cutting of the specimen(s) has taken place, the cutting operation itself is started by means of the appropriate key 24 on the operating panel 22 (or, as an alternative, automatically). The number of cuts to be carried out can be preselected on the operating panel 22.

Furthermore, there is provision for it to be possible, in the case of a plurality of objects 6–6c present on the disk 7, to use the operating panel 22 to preselect individual objects for cutting or to establish a sequence of the objects 6–6c to be cut. For this purpose, the respective position of the cutting blade or of the feed carriage 9 after the initial cut of the objects has taken place is stored as the 0 position.

This can can [sic] be established, for example, by counting the individual steps for activating the stepper motor 13 in the control circuit or by providing an additional encoder for determining the position of the feed carriage 9.

During the cutting operation, the control circuit 14 is used to feed the cutting blade 4 from this stored 0 position onto the selected object or objects 6–6c and to return it to this 0 position after the cutting operation has taken place. The position of the objects or the rotational position of the disk 7 with respect to the cutting blade 4 is continuously determined by the angle-position encoder 15. There is provision for the rotational speed of the disk 7 to be higher outside the cutting operation than during the cutting operation. This results in a rapid feed of the object toward the cutting blade, combined with an advantageous slow cutting movement during the cutting operation.

Individual objects 6–6c for cutting can be preselected either simultaneously or successively by means of the operating panel 22 and the control circuit 14. As a result, once a microtome 1 has been fitted, it can be used to automatically produce a multiplicity of cut sections without the operator having to intervene in the cutting operation. This is highly advantageous in particular if the microtome is arranged, for example, in an encapsulated cryostat. Changing an object in cryostats is a very time-consuming operation, since in most cases the cryostat has to be defrosted and the cold lost when the equipment is opened must first be compensated for.

Of course, it also lies within the scope of the present invention to arrange only a single object holder 6 on the disk instead of the four object holders described. It has proven advantageous if a particular changeover position is always automatically adopted, via the control circuit, when changing an object, for example after pressing a key on the control panel. This changeover position is at the 3 o'clock position, corresponding to the position of the object holder 6a in FIG. 7b. As a result, the specimen is changed as far away from the blade 4 as possible, thus minimizing the risk of injury. Naturally, the object holder or specimen can also be changed automatically in this defined changeover position.

An interface 26, via which an external computer 28 can be connected via a control line 27, is provided on the operating panel 22 or, alternatively, on the control circuit 14 in order to integrate the disk microtome 1 in a higher-priority unit, for example a cryostat. The external computer 28 can then take over the functions of the operating panel 22. Stored programs can then be used to automatically control all the functions of the disk microtome 1 and, in addition, the further functions of higher-priority units, such as for example a cryostat.

FIG. 7b shows a side view of the exemplary embodiment in accordance with FIG. 7a, with the four objects 6 and 6a–6c arranged on the disk. Of course, it is possible to arrange a different number of objects on the disk. However, it has been found that it is advantageous for the objects to be arranged symmetrically on the disk, in order to avoid any unbalance when the disk rotates. Otherwise, appropriate balancing weights have to be arranged on the disk in order to compensate for the unbalance. This may be achieved, for example, by arranging a balancing weight of this nature in a displaceable manner on the disk. In this case, the direction of displacement may extend from the rotary shaft 16 toward the edge of the disk 7. If, in an arrangement of this nature, the balancing weight is preloaded by means of a spring, it is possible for the unbalance to be corrected automatically, substantially independently of the mass of the object to be cut. Furthermore, it is, of course, also possible for the balancing weight to be arranged displaceably on the edge of the disk 7.

The automatic/motor-driven functions which have been described with reference to the exemplary embodiment in accordance with FIG. 7a are not, of course, limited to this design, but rather can be transferred analogously to the other exemplary embodiments. Naturally, it is also possible to use individual automatic/motor-driven functions for the other types of microtome.

Furthermore, it is possible to provide the cutting blade on the disk and the object holder or holders on the base. Moreover, the disk itself may also be designed as a blade, in which case the cutting operation is carried out by a movement of the disk or by a movement of the object.

In a further configuration of the invention, the object holders may also be arranged next to one another in the direction of the rotary shaft of the disk. In this case, individual objects or a plurality of objects can be cut simultaneously or successively at different cutting speeds.

In a further configuration of the invention, a cut distance device which is known per se is provided on the blade holder of the microtome. This device is assigned one or more conveyor belts which are moved by means of a drive motor. The motor or motors may be electrically connected to the control circuit or the computer unit so that they can be supplied with power as a function of the preselected program in order to carry out automatic process control.

The rotating component is described and illustrated in the exemplary embodiments as disk 7. Of course, the scope of the invention also encompasses the use of a rotating arm or the like instead of a disk. However, it is advantageous, for safety reasons, if the rotating component has at least one cover, for example in the form of a disk.

What is claimed is:

1. A microtome for producing thin-cut sections for microscopy from an object to be cut, comprising:
    a base designed to lie substantially horizontally in use;
    a cutting blade:
    a blade holder carried by the base for holding the cutting blade;
    an object holder carried by the base for holding the object which is to be cut, the cutting blade and object holder being mounted on the base in a manner that permits a cutting operation to be carried out by means of a relative movement between the object and the cutting blade in a plane,
    a rotating component having an axis of rotation and defining a plane of rotation generally perpendicular to the axis of rotation, wherein one of the cutting blade and object holder is mounted on the rotating component in order to generate the relative movement, and wherein the rotation axis of the rotating component is arranged obliquely with respect to the base;
    a drive motor for the rotating component;
    a feed carriage mounted on the base for linear movement, the feed carriage carrying one of the cutting blade and object holder, whereby the linear movement sets the cutting thickness;
    a feed motor operatively connected for moving the feed carriage; and
    a control circuit connected to the feed motor for controlling the movement of the feed carriage with respect to the base.

2. A microtome according to claim 1, wherein the axis of rotation of the rotating component forms an angle with the base approximately in the mid region between horizontal and vertical.

3. A microtome according to claim 1, wherein the object holder is arranged on the rotating component and the blade holder is arranged on the feed carriage.

4. A microtome according to claim 1, wherein the blade holder is arranged on the rotating component and the object holder is arranged on the feed carriage.

5. A microtome according to one of claim 1, wherein the object holder is arranged on the rotating component and the rotating component is mounted on the feed carriage.

6. A microtome according to claim 1, wherein the blade holder is connected to the feed carriage.

7. A microtome according to claim 1, wherein the drive motor is connected to the control circuit and the control circuit selectively controls the speed of the drive motor.

8. A microtome according to claim 1, wherein the object holder is connected to the feed carriage in order to set the cutting thickness.

9. A microtome according to claim 1, wherein the feed motor moves the feed carriage longitudinally with respect to the base.

10. A microtome according to claim 1, wherein the feed motor moves the feed carriage perpendicularly with respect to the base.

11. A microtome according to claim 1, wherein the feed motor moves the feed carriage obliquely with respect to the base.

12. A microtome according to claim 1, wherein the rotating component comprises a disk.

13. A microtome according to claim 1, wherein a plurality of object holders are arranged next to one another on the rotating component.

14. A microtome according to claim 1, wherein a plurality of object holders, which are arranged next to one another in the radial direction are provided on the disk, so that a plurality of objects are cut simultaneously.

15. A microtome according to claim 1, wherein the control circuit is electrically connected to an operating panel.

16. A microtome according to claim 1, further comprising at least one balancing weight for compensating for imbalance of the rotating component due to at least one object mounted thereon.

17. A microtome according to claim 7, wherein the control circuit selects the speed of the drive motor as a function of rotational position of the rotating component.

18. A microtome according to claim 17, further comprising an angle-position encoder assigned to the rotating component and the angle-position encoder is electrically connected to the control circuit.

19. A microtome according to claim 18, wherein a starting point of the cutting operation is registered by the angle-position encoder.

20. A microtome according to claim 19, wherein the control circuit selects a first cutting thickness at the starting point of the cutting operation and a second cutting thickness for the performance of the cutting operation.

21. A microtome according to claim 7, wherein the control circuit selects a fixed angular position of the rotating component in response to user selection of a change-blade position.

22. A microtome according to claim 7, wherein the control circuit selects the speed of the drive motor as a function of the material from which the object to be cut is comprised.

23. A microtome according to claim 7, wherein the control circuit selects the speed of the drive motor as a function of cutting thickness chosen for the object to be cut.

24. A microtome according to claim 9, wherein the axis of rotation of the rotating component forms an angle with the base sufficient to decrease the relative distance between the cutting knife and the object to be cut by a distance substantially less than the distance that the feed motor moves the feed carriage.

25. A microtome according to claim 10, wherein the axis of rotation of the rotating component forms an angle with the base sufficient to decrease the relative distance between the cutting knife and the object to be cut by a distance substantially less than the distance that the feed motor moves the feed carriage.

26. A microtome according to claim 12, wherein the disk and the cutting blade are inclined with respect to the base at approximately the same angle.

27. A microtome according to claim 26, wherein the angle of inclination is of a magnitude that an operator can operate the microtome comfortably while seated in front of the microtome.

28. A microtome according to claim 13, wherein a single object or the series of objects to be cut can be individually preselected using the control circuit.

29. A microtome according to claim 28, wherein the control circuit preselects different cutting thicknesses for a single object or different cutting thicknesses for a plurality of objects.

30. A microtome according to claim 15, wherein the control circuit or the operating panel has an interface for connection to a computer unit.

31. A microtome according to claim 30, wherein the computer unit is programmed with a program for automatic process control.

32. A microtome according to claim 16, wherein the balancing weight is displaceable.

* * * * *